(12) United States Patent
Bruch et al.

(10) Patent No.: US 7,816,149 B2
(45) Date of Patent: Oct. 19, 2010

(54) NANOBIOPROCESSOR FOR PROTEIN AND CELL THERAPY

(75) Inventors: Reinhard Bruch, Reno, NV (US); Jutta Gietl, Reno, NV (US)

(73) Assignee: Applied Photonics Worldwide, Inc., Reno, NV (US)

( * ) Notice: Subject to any disclaimer, the term of this patent is extended or adjusted under 35 U.S.C. 154(b) by 1568 days.

(21) Appl. No.: 11/093,460

(22) Filed: Mar. 29, 2005

(65) Prior Publication Data

US 2005/0214380 A1    Sep. 29, 2005

Related U.S. Application Data

(60) Provisional application No. 60/557,141, filed on Mar. 29, 2004.

(51) Int. Cl.
*G01N 33/551* (2006.01)

(52) U.S. Cl. .................... 436/524; 436/525; 436/805

(58) Field of Classification Search ................. 436/524, 436/525
See application file for complete search history.

(56) References Cited

U.S. PATENT DOCUMENTS

| | | | |
|---|---|---|---|
| 5,223,482 A | 6/1993 | Schilling, Jr. et al. | |
| 5,434,050 A | 7/1995 | Maggio et al. | |
| 5,795,963 A | 8/1998 | Mullan | |
| 5,891,887 A | 4/1999 | Markwell et al. | |
| 5,912,410 A | 6/1999 | Cordell | |
| 5,990,479 A | 11/1999 | Weiss et al. | |
| 6,011,001 A | 1/2000 | Navia et al. | |
| 6,172,043 B1 | 1/2001 | Ingram et al. | |
| 6,175,057 B1 | 1/2001 | Mucke et al. | |
| 6,306,610 B1 * | 10/2001 | Bawendi et al. | 435/7.1 |
| 6,326,144 B1 | 12/2001 | Bawendi et al. | |
| 6,346,431 B1 | 2/2002 | Yoo et al. | |
| 6,359,112 B2 | 3/2002 | Kapurniotu et al. | |
| 2002/0162995 A1 | 11/2002 | Petroff et al. | |
| 2003/0087809 A1 | 5/2003 | Tsai | |
| 2003/0166898 A1 | 9/2003 | Chopra et al. | |
| 2004/0258705 A1 | 12/2004 | Zabrecky et al. | |

* cited by examiner

*Primary Examiner*—Christopher L Chin
(74) *Attorney, Agent, or Firm*—Mintz, Levin, Cohn, Ferris, Glovsky and Popeo, P.C.

(57) ABSTRACT

A nanobioprocessor for protein and cell therapy comprises a selectively coated quantum dot having selected band gap energies, characteristic absorption, emission spectra and outer coatings for therapy and diagnostic purposes in biophotonics and nanomedicine, and an electromagnetic radiation and detector source configured to remotely heat and/or selectively excite the quantum dot to associate with target specific misfolded or anomalous proteins, diseased cells and tissue.

20 Claims, 5 Drawing Sheets

NANOBIOPROCESSOR FOR PROTEIN AND CELL THERAPY

CROSS REFERENCE TO RELATED APPLICATIONS

This application claims the benefit of the priority of U.S. Provisional Application Ser. No. 60/557,141, filed Mar. 29, 2004 and entitled "NANOBIOPROCESSOR FOR PROTEIN AND CELL THERAPY".

BACKGROUND

The subject matter described herein is related to biomedical nanotechnology combining multifunctional nanoparticles with biological materials such as proteins and cells.

Tiny nanocrystals, so called quantum dots, can be designed in size, shape and consistency to render a wide range of thermal and optical properties. The key to progress in nanobiotechnology is the confinement of electrons in a spatial region on the order of a few nanometers to a few tens of nanometers. When an electron is confined to such a small volume, its energy spectrum becomes discrete or at least close to that, while in bulk semiconductor material the energy is quasi-continuous. In order to exhibit the desired discreteness of the vibrational and excitation spectrum, the size of the confinement must be comparable to the Bohr radius of the quasi-bound entity, named exciton, of an electron and its hole. Controlling the size and shape of QDs allows the modeling and engineering of its optical properties in a wide range, e.g. the energies at which absorption and emission will preferentially occur.

Several human and/or animal diseases such as Alzheimer's, Huntingtons, Lou Gehrig's, Jakob-Kreutzfeld and Mad Cow disease are associated with protein misfolding, creating a plaque of abnormally shaped proteins, sticking together and destroying their proper three dimensional structure. These proteins form aggregates of insoluble gunk and in this process they may devastate the brain cells. Some of these proteins "prions" are infectious, causing mad cow disease and its human counterpart Jakob-Creutzfeld disease. For example, Alzheimer's disease affects the brain by destroying the neurons. Two distinctive characteristics of Alzheimer's disease are amyloid plaques and neurofibrillary tangles. Thus, amyloid plaques are abnormal aggregations of tissue that consists mainly of a protein called β-amyloid. These amyloid plaques from individuals with Alzheimer's disease show dominance of β-sheet structures indicated by the amide I and amide II band structures.

DESCRIPTION OF THE RELATED ART

Weiss, et al. in U.S. Pat. No. 5,990,479 describes a luminescent semiconductor nanocrystal device, which is capable of linking to an affinity molecule. The compound comprises a semiconductor nanocrystal emitting electromagnetic radiation (luminescing) and at least one linking agent. U.S. Pat. Nos. 6,306,610 and 6,326,144 by Bawendi, et al. entitled "Biological applications of quantum dots" provide a fluorescent semiconductor nanocrystal associated to a compound, wherein the nanocrystals have a characteristic spectral emission, wherein said spectral emission is tunable to a desired wavelength by controlling the size of the nanocrystal, and wherein said emission provides information about a biological state. Furthermore Bawendi, et al. have also described soluble fluorescent nanocrystals capable of light emission, including a quantum dot having a selected band gap energy, a layer over coating the quantum dot, the over coating layer comprised of a material having a band gap energy greater than that of the quantum dot, and an organic outer layer, the organic layer comprising a compound having a least one linking group for attachment of the compound to the over coating layer and at least one hydrophilic group space apart from the linking group by a hydrophobic region sufficient to prevent electron charge transfer across the hydrophobic region. The coated nanocrystal exhibits photoluminescence having quantum yield of greater than 10% in water.

"Quantum dot infrared detection device and fabrication of the same", U.S. Pat. No. 6,346,431 to Yoo et. al describe a new concept of detection device. However, Yoo does not contemplate nanomedicine applications. In U.S. Pat. No. 6,346,431 to Melver et al, "Composite quantum well infrared detector" does not contemplate application in biophotonics. Furthermore, in U.S. Pat. App. No. U.S. 2002/0162995 A1 by Petroff et al, "Mid infrared and near infrared light upconvereter using self-assembled quantum dots" describes a method and device which converts light from a first wavelength to a second wavelength.

U.S. Pat. No. 5,223,482 by Schilling, Jr. et al., "Recombinant Alzheimer's protease 10 inhibitory amyloid protein and method of use" describes DNA sequences encoding beta-amyloid related proteins associated with Alzheimer's disease. Also provided therein is a DNA sequence encoding, a novel protease inhibitor. In addition in the U.S. Pat. No. 5,434,050 by Maggio, et al.," Labeled beta-amyloid peptide and methods of screening for Alzheimer's disease" provides a labeled beta-amyloid peptide of active fragment; a composition including the labeled beta-amyloid peptide or active fragment thereof and a pharmaceutical carrier.

Moreover an "Amyloid precursor protein in Alzheimer's disease" was claimed in U.S. Pat. No. 5,795,963 by Mullan. This arrangement provides an isolated nucleic acid characteristic of human amyloid precursor protein. It also provides a method of diagnosing or predicting a predisposition to Alzheimer's disease. Another method of enhancing amyloid precursor protein processing along a non-amyloidogenic pathway in patients suffering from, or at risk of developing, Alzheimer's disease and a method of treatment or prophylaxis of Alzheimer's disease was described in U.S. Pat. No. 5,891,887 by Markwell et al.

Furthermore, in U.S. Pat. No. 5,912,410, "Transgenic non-human mice displaying the amyloid-forming pathology of Alzheimer's disease", by Cordell, a method is described in which cloned recombinant or synthetic DNA sequences related to the pathology of Alzheimer's disease are injected into fertilized mammalian eggs (preferably mouse eggs). The injected eggs are implanted in pseudo pregnant females and are grown to term to provide transgenic mice whose cells express proteins related to the pathology of Alzheimer's disease. Another method of protein therapy by orally administering cross-linked protein crystals has been described in U.S. Pat. No. 6,011,001 by Navia, et al. Where a protein such as an enzyme or antibody is immobilized by, cross linking crystals of the protein with a multifunctional cross-linking agent.

Moreover, treatments for neurotoxicity in Alzheimer's disease caused by beta amyloid peptides are discussed in U.S. Pat. No. 6,172,043 by Ingram, et al. This arrangement involves identification of a mechanism of beta-amyloid peptide cytotoxicity that enables treatment of conditions caused by beta-amyloid peptide aggregates by administration of compounds, which antagonize the mechanism of cytotoxicity.

U.S. Pat. No. 6,175,057 by Mucke, et al., "transgenic mouse model of Alzheimer's disease and cerebral amyloid angiopathy" is described in which non-human transgenic animal models are used for Alzheimer's disease. Finally, Kapurniotu, et al. in U.S. Pat. No. 6,359,112 entitled, "Peptides used as agonists and/or inhibitors of amyloid formation and cytotoxicity and also for use in Alzheimers disease, in type II diabetes mellitus and in spongiform encephalophathies" discloses that certain peptide molecules can be used as the basic structures (template molecules) for inhibiting and analyzing amyloid formation and cytotoxicity in amyloid illnesses. These references are based on immunogenic peptides like β-amyloid peptide protein using numerous biochemical pathways for enhancing immunity, inhibiting and treatment of Alzheimer's disease. But none of these methods is based on nanotechnology in particular, the usage of encoded quantum dots for protein therapy.

U.S. Pat. App. No. US020030087809A1 to Tsai discusses using lectin or lectin-like molecules to promote oligomerization of a glycoprotein or an immunologically and/or biologically active complex comprising glycoproteins. In particular, this arrangement provides compositions of a molecular complex comprising lectin molecules and immunologically and/or biologically active molecules. Methods of making such molecular complexes and methods of use of the compositions comprising such molecular complexes for the prevention and treatment of diseases, particularly cancer and infectious diseases, and for eliciting an immune response in a subject, are also provided.

U.S. Pat. App. No US020030166898A1 to Chopra describes a MOGp protein which is a member of the Ig superfamily. In particular, isolated nucleic acid molecules are provided encoding the human MOGp protein. MOGp polypeptides are also provided as are vectors, host cells and recombinant methods for producing the same. Also provided are diagnostic and therapeutic methods for detecting and treating cancer, inflammation, and multiple sclerosis (MS).

U.S. Pat. App. No. US020040258705A1 to Zabrecky discusses using lectin or lectin-like molecules to promote oligomerization of a glycoprotein or an immunologically and/or biologically active complex comprising glycoproteins. In particular, this arrangement provides compositions of a molecular complex comprising lectin molecules and immunologically and/or biologically active molecules. Methods of making such molecular complexes and methods of use of the compositions comprising such molecular complexes for the prevention and treatment of diseases, particularly cancer and infectious diseases, and for eliciting an immune response in a subject, are also described.

SUMMARY

The nanoparticles described herein represent a new class of biophotonic systems that may serve as both diagnostic and treatment agents in nanomedicine. These nanoparticles may provide nanomachines with controlled release of specific energy, radiation and/or particles, diagnostic agents, proteins, genes, DNA and drugs for protein and cell therapy. The nanodevices may reversibly denature a single β-sheet of a protein, while leaving the rest of the protein intact or generally causing a misfolded protein to properly fold by determination of the electronic structure, energies and potential, vibrational properties and thermal transport coefficients of quantum dots (QDs) and their protein and macromolecular counterparts such as peptides. As a result, the subject matter described herein may advance the design and application of QDs towards correcting misfolded protein structures including glycoproteins by exploiting their thermal properties and thermal transport properties of proteins with the ultimate goal to engineer and develop a nanobioprocessor for protein and cell therapy.

A nanobioprocessor for protein and cell therapy may comprise a selectively coated quantum dot having selected band gap energies, characteristic absorption, emission spectra and outer coatings for therapy and diagnostic purposes in biophotonics and nanomedicine, and an electromagnetic radiation and detector source configured to remotely heat and/or selectively excite the quantum dot to associate with target specific misfolded or anomalous proteins, diseased cells and tissue.

In some variations, the nanoparticles may represent a new class of biophotonic sensor systems or nanomachines that work in the near infrared (NIR) range which can both serve as superior and stable diagnostic and treatment agents in nanomedicine because of low losses in human cells and tissue. Such nanoparticles may provide controlled release of specific energy, radiation and/or particles, diagnostic agents, proteins, genes, DNA and drugs with great potential for protein and cell therapy.

The quantum dot may be comprised of materials having selected band gap energies in the NIR regions and it may have a quantum dot surface that specifically binds to diseased cells, tissues or proteins.

In some variations, the quantum dots are coated with lipid layers. Such lipid layers make the quantum dots hydrophilic and additionally enhance their motion in the bloodstream.

The quantum dot may include gold particles or gold coated particles with absorption and emission spectra in the NIR region that can be activated by laser pulses to induce heating of the quantum dots and its environment.

The radio source may be chosen from a group comprising: NIR infrared diode laser, vertical cavity surface emitting laser, or vertical cavity surface emitting array laser. In some variations, such a laser may be tunable in the NIR range.

In some variations, the quantum dot may be adjacent to a misfolded protein anomalous biomolecule having a confirmation that can be changed through at least one of remote vibrational or electronic energy transfer. Additionally or in the alternative, the quantum dot may be adjacent to a misfolded glycoprotein having a confirmation that can be changed through at least one of remote vibrational or electronic energy transfer.

The nanobioprocessor may also comprise a beta-amyloid coupled to or adjacent to the encoded quantum dot, and a coded peptide channel for transformation of a misfolded beta-amyloid protein to an alpha-helical conformation or denaturing of other biological systems with peptide bonds.

The naniobioprocessor may be used to treat a variety of conditions including, but not limited to: Alzheimer's Disease, Huntington's disease, Lou Gehrig's disease, Creutzfeld-Jacob disease and other related diseases. The nanobioprocessor may also be configured to treat different types of cancers due to degradation of the glycoproteins at the cell membrane level.

The nanobioprocessor quantum dots may be composed with a core of nanocrystals sensitive in the NIR region. Such nanocrystals may be chosen from a group comprising: Pb based-cores, Lead Sulphide (PbS), Lead Selenide (PbSe), Lead Telluride (PbT), or Titanium Oxide.

In yet another variation, the nanobioprocessor may further comprise a micromirror spectrometers for the determination and detection of the constituents and in-vivo diagnostics. The nanobioprocessor may also provide that the local heating and energy transfer destroys or conforms diseased cells and proteins and also for drug delivery with nanocapsules.

In some variations, a nanobioprocessor for protein and cell therapy may comprise a selectively coated quantum dot composed of various materials including a quantum dot core of spherical shape and structure made of different materials in which the core material partially determines the range of an emission. However, difference in the core size determines the final fluorescence emission characteristics of the quantum dot. The nanocrystals cores need a protective coating for their surroundings.

For biological applications polymer or polymer mixtures or lipid surfaces may be used to further protect them and render them water soluble. The final coating like lipid layers provides also the linking with various biological molecules such as additional proteins, antibodies, DNA etc. Furthermore, polystyrene beads of several micron diameters are utilized to simultaneously house different quantum dots where the beads are conjugated to specific biological probes to enable multiplexed cellular assays. Using these procedures, the QD's are associated with selected bandwidth energies and characteristic absorption and emission spectra for therapy and diagnostic purposes. Therefore, they may be exposed to electromagnetic radiation sources including laser diodes and tunable lasers as well as microwave sources to remotely heat and excite the QD's in and around the biological systems.

One other variation, uses QD light emission and/or radiation transfer specific misfolded proteins, diseased cells, tissue and body fluids as well as specific other biological agents can be targeted. Especially, to monitor the QD-protein, QD-cell and QD-cell interaction nanospectroscopy is used. In particular there is much interest in developing the QD's with stable emission in the near infrared (NIR) because these wavelengths are minimally absorbed by biological tissue. NIR sensitive QD's, for example Pb based cores composed of Lead Sulphide (PbS), Lead Selenide (PbSe) and Lead Telluride (PbTe) materials are utilized. These dots cover the telecom range of emission and detection upto about 3 microns. For Biological applications additional water soluble layers such as lipid bilayers have to be applied. For detection in the NIR wavelength range ultra compact micromirror spectrometers may be utilized.

Another variation of the subject matter described herein utilizes NIR sensitive QD's in the transformation of secondary structure of protein, while leaving the rest of the protein intact or generally causing a misfolded protein to properly fold by determination of the electronic structure, energies and potential, vibrational properties and thermal transport coefficients of Quantum Dots and their protein and macromolecular counterparts such as peptides. In some variations, the subject matter herein may be used to advance the design and application of QD's towards correcting misfolded protein structures by exploiting their thermal properties and thermal transport properties of proteins with the ultimate goal to engineer and develop a nanobioprocessor for protein and cell therapy.

BRIEF DESCRIPTION OF THE ACCOMPANYING FIGURES

The subject matter described herein is described with reference to the figures, which are presented for the purpose of illustration only, and in which.

Figure 8:
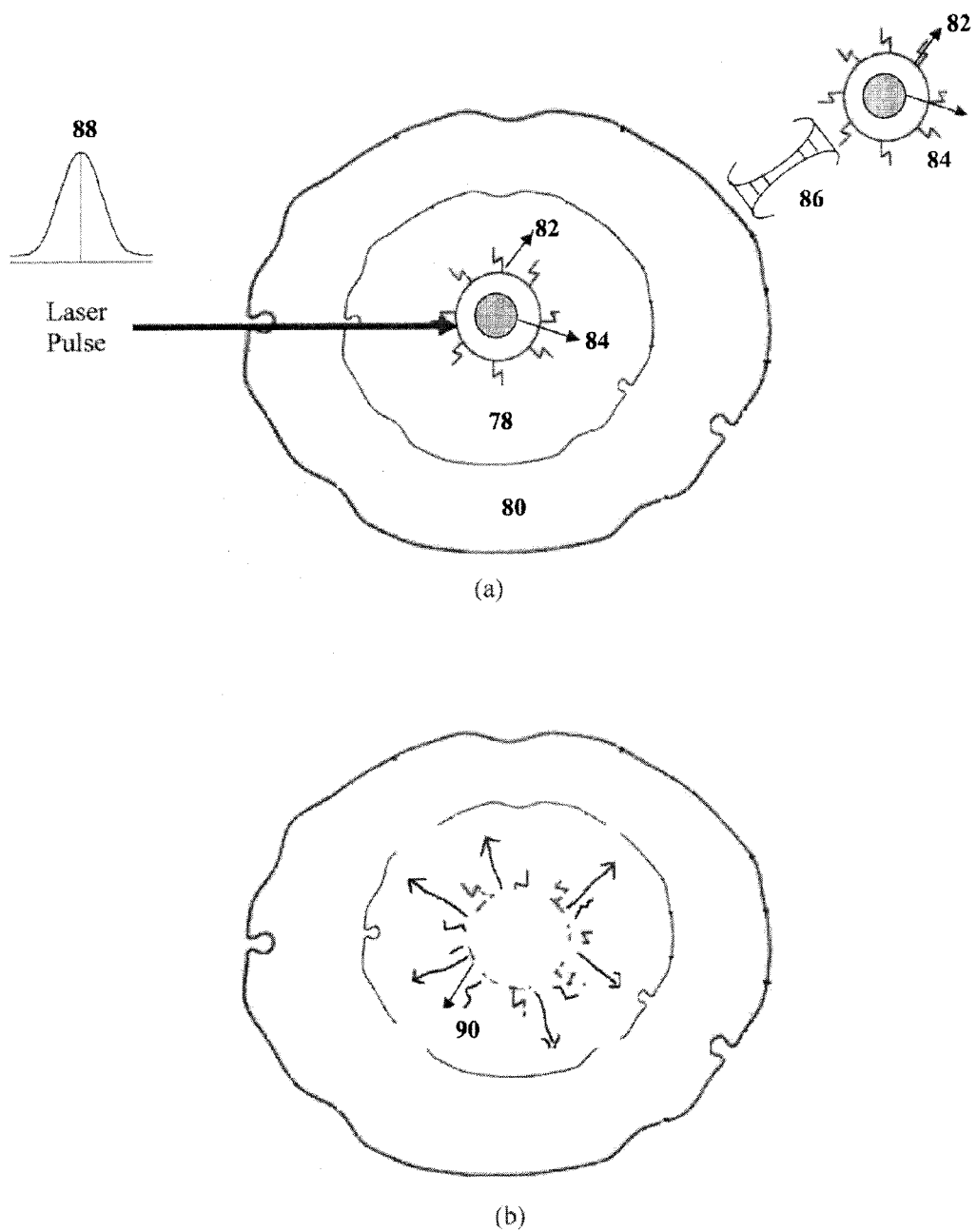

FIG. 8(a) illustrates a single cell with a quantum dot inside and another quantum dot attached to its membrane surface. Also indicated is a laser pulse propagating towards the cell center hitting the QD; and FIG. 8(b) illustrates a laser pulse that has heated the quantum dot which is in the phase of explosion or disintegration destroying the cell by energy transfer or releasing a drug through nanocapsule.

DETAILED DESCRIPTION

The subject matter described herein is directed to heating and controlling the temperature of a quantum dot remotely via energy and/or radiation transfer. This technique permits the application of QDs to molecular cell biology and protein therapy beyond their application as optical probes.

Figure 1:
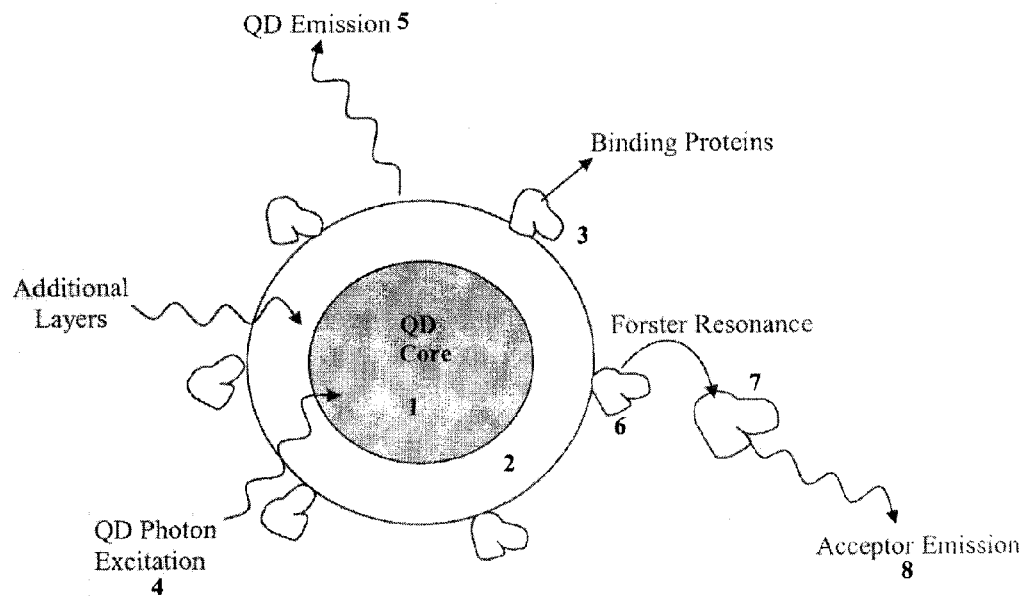
FIG. 1 is a schematic of a quantum dot composed of a core and outer layers with binding proteins; also shown are the QD excitation, emission and Foerster's resonance processes with acceptor emission.

FIG. 1 shows a schematic of a typical quantum dot, comprised of a core 1, additional coated layers to protect the core and make them water soluble 2. Also shown are binding proteins 3, photon excitation 4, the QD emits at a different wavelength 5 and non-radiatively transfers energy 6 to a fluorescent dye molecule 7, where the acceptor emission occurs at a different wavelength 8.

Figure 2:
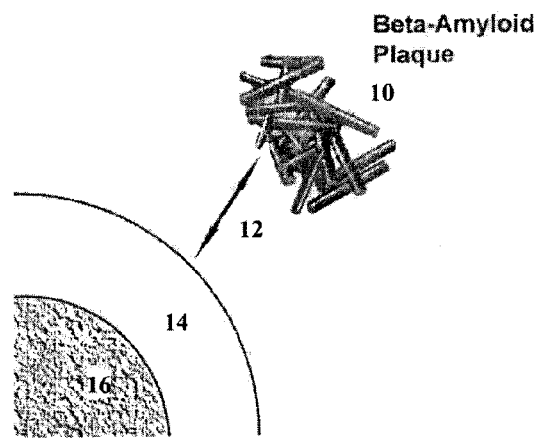
FIG. 2 is a schematic illustration of a β-amyloid plaque in the vicinity of a cell membrane.

FIG. 2 displays a beta-amyloid plaque 10, which is one of the major causes of Alzheimer's disease (AD). This plaque is in the neighborhood of a nerve cell membrane 14 and the interior of a nerve cell 16. Number 12 represents a type of peptide channel where the beta-amyloid plaque interacts with the cell surface. Misfolded proteins are responsible for many human and animal diseases.

Figure 3:
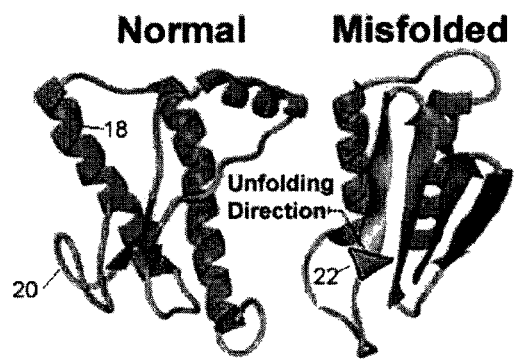
FIG. 3(a) is a schematic illustration of a healthy protein that folds itself into a series of a like helixes and a misfolded protein that rearranges a portion of itself into a β-sheet.
FIG. 3(b) is a schematic which illustrates an example of GPI-linked protein can be Thy 1 which is the T-cell marker (that interacts with proteoglycans in the extracellular matrix (ECM))
Figure 3:
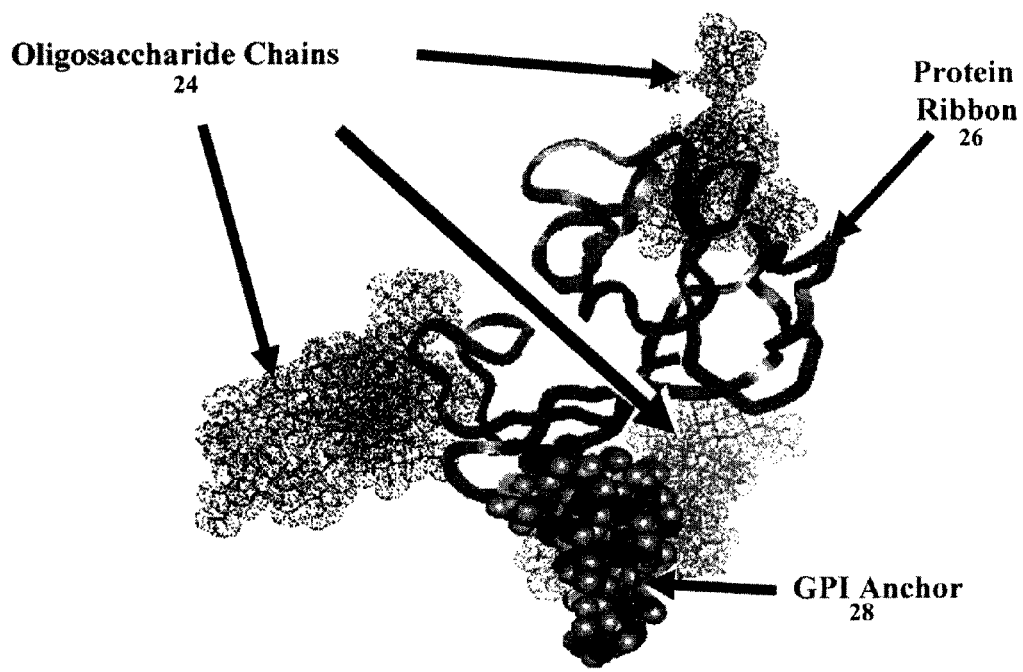

In FIG. 3(a), a schematic example of model protein structures is shown that is expressed on the cell surface in a wide variety of animal and human tissues. Both the normal and abnormal (misfolded) proteins may be derived from the same gene and also have the same amino acid sequence. However, the conformation is different with misfolded structures 20 primarily alpha helical 18 and predominantly beta sheets 22, where the unfolding direction is indicated.

In FIG. 3(b) an example of GPI-linked protein can be Thy 1 which is the T-cell marker as shown. It interacts with proteoglycans in the extracellular matrix (ECM). In the structure indicated 24 relates to the oligosaccharide chains 26 to the protein ribbon and 28 GPI anchor.

Figure 4:
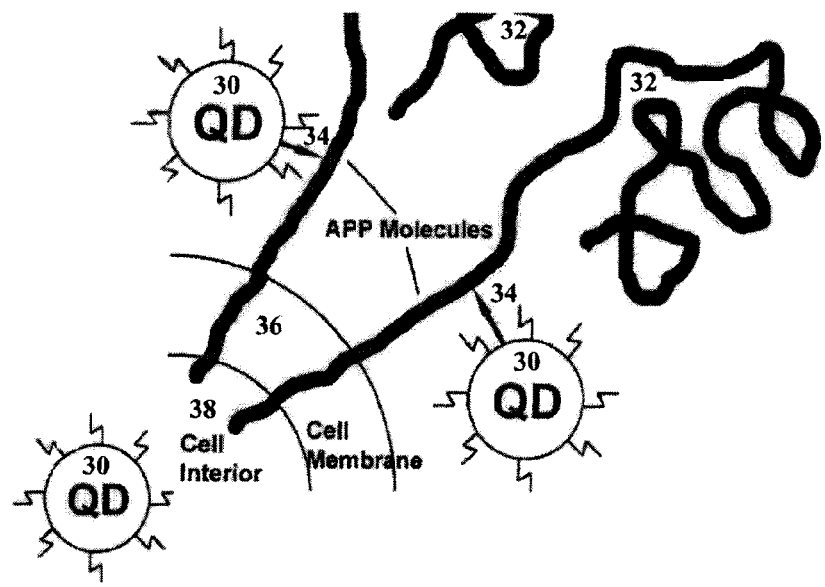
FIG. 4 is an illustration of quantum dots embedded and/or in the vicinity of APP molecules.
Figure 5:
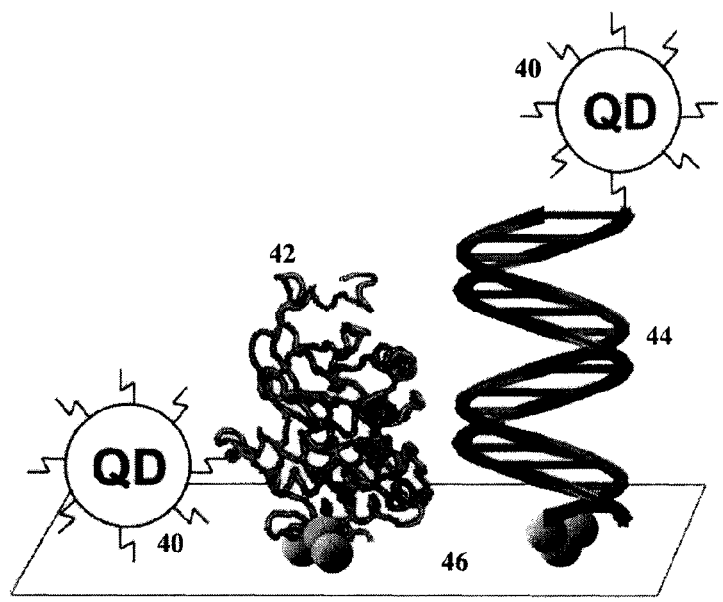
FIG. 5 is a schematic illustration of a quantum dot interacting with a protein and a DNA complex system attached to a substrate.
Figure 6:
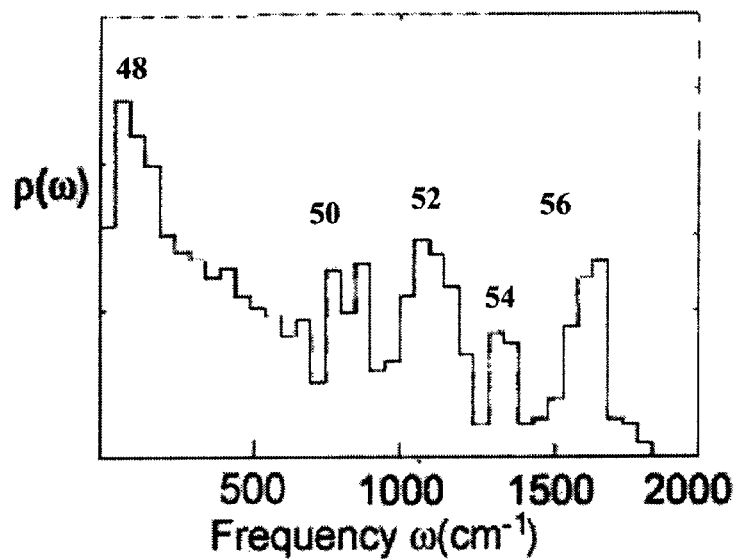
FIG. 6 is an illustration of the normal mode density, ρ, such as myoglobin in the frequency domain from 5 cm-1 to about 1900 cm-1.
Figure 7:
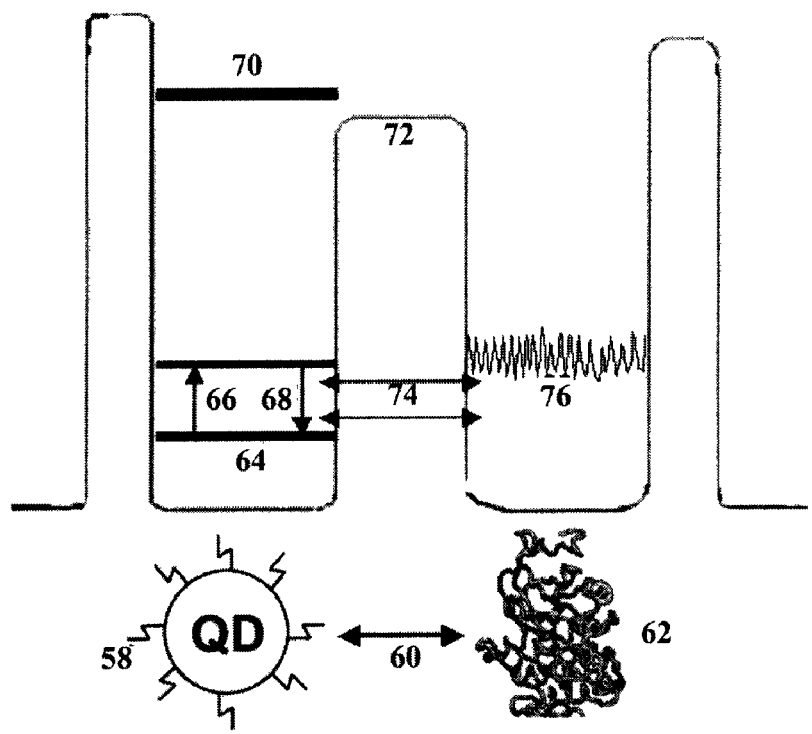
FIG. 7 is an illustration of a quantum dot attached to a protein molecule. Shown is the possible mechanism of heat transfer, excited states of the QD, absorption and emission processes as well as the vibrational coupling.

With reference to FIG. 4, a QD 30 implanted into biological tissue cells 38 and/or attached to biological molecules such as amyloid precursor protein (APP) 32 attached to the cell membrane 36 is shown. The APP molecule is a protein that may help neurons grow and survive. Hence APP may help damaged neurons repair themselves and may help parts of neurons grow after brain injury. In AD, some processes cause APP to be snipped into fragments, one of which is called beta-amyloid; the beta-amyloid fragments eventually clump together into plaques. The APP is associated with the cell membrane, the thin barrier that encloses the cell. After it is produced, APP sticks through the neuron's membrane 36, partly inside 38 and partly outside the cell. The beta-amyloid fragments begin coming together into clumps outside the cell, and then join other molecules and non-nerve cells to form insoluble plaques 10 (see FIG. 2).

A major aim of the subject matter described herein is to utilize QDs 30 towards correcting misfolded structures through localized heating via encoded peptide channels 34. The power needed to provide excess heat for structural change depends on the ability of the neighboring biological molecule to reestablish thermal equilibrium. This process depends on the thermal diffusivity and coefficient of thermal conductivity of proteins, which have been tested on small, globular proteins. According to the subject matter described herein, this method will be applied to transform the conformation of the Alzheimer's amyloid β-peptide and other bioagents.

Another variation of the subject matter described herein is the heat transfer technique from QDs 40 to proteins 42 and DNA 44. This process is schematically indicated in FIG. 5, where 46 represents a substrate, on which the protein and DNA are attached. Different molecular species can be attached to different quantum dots selectively coated by specific peptides (see, for example, "Scientists activate neurons with quantum dots", EE Times, Dec. 6, 2001). Another application of the subject matter described herein is to use selectively encoded and coated quantum dots in the vicinity of a protein channel as an effective sources of heat transfer via vibrational modes to change the conformation of proteins such as amyloid plaques, or to attach these QDs directly with the cell surface to trigger specific reactions. It is also within the scope of the subject matter described herein to modify DNA by embedded QDs also displayed in FIG. 5. In particular, water soluble, nontoxic, coated semiconductor nanocrystals including a QD having a selected band gap energy and peptide bond attachment as a linking mechanism is important in the context to change the nature of proteins, DNA, cells and other bioagents.

One representation of the subject matter described herein is conformational changes in bio-molecules by inductive and or optical coupling to the attached QD. Heat is transported in a macromolecule such as a protein by its vibrations. The size and temperature of a QD plays a large role in controlling structural changes at a molecular level for thermal equilibration. FIG. 6 is a schematic representation of the vibrational mode density of a biological molecule in this case myoglobin. As can be seen from FIG. 6, the large majority of the modes are localized in major areas 48, 50, 52, 54, 56 where the band structure 56 represents the amide-I and amide-II region.

A further important example useful for understanding and implementing the subject matter described herein is displayed in FIG. 7. This figure exhibits a schematic representation of a QD 58 with an attached protein 62 via a peptide encoded or quantum wire channel 60 which will allow transfer of vibrational energy similar to an optical wave-guide. Such quantum dots exhibit various energy states 64, 70. In FIGS. 6, 66 and 68 characterize optical absorption and emission processes and the dependence on the confining QD potential. Therefore, the phonon spectrum of a nanocrystal and its molecular environment is also quantized and produce phonon bands leading to broadening of the shown excited states.

Furthermore, thermal relaxation may occur via the phonons provided that the electronic states of the QD couple to the oscillations of the wall of the confining potential well. This may warrant the introduction of potentials, which fluctuate in time due to lattice vibrations. High lying electronic states are most suited to polarize the lattice of the wall efficiently, 70, 72; they represent the channel environment and 74 represents the encoded peptide channel which couples the QD with the protein quantum well structure. The label 76 represents vibrational states of the protein molecule attached to the QD. These vibrational bands are affected by the vibrational coupling of the two complex quantum systems. Any heat transfer mechanism engineered by optimizing the energy levels of the QD depending on the size of the quantum well and the material properties can enhance the denaturing and/or transformation processes of specific protein structures and cells, as described above.

FIG. 8(*a*) shows a single cell comprised of cell nucleus 78 with the 80 lipid membrane layer and a quantum dot inside 82 which encloses a nanocapsule 84 containing a drug. Also shown is a quantum dot and nanocapsule in 82 and 84 respectively attached to its cell membrane surface via conjugate bonds 86. Also indicated is a laser pulse 88 propagating towards the cell center hitting the QD. In FIG. 8*b*) the laser pulse has heated the quantum dot which is in the phase of explosion or disintegration destroying the cell by energy transfer or releasing a drug through nanocapsule 90.

Due to the extremely small size of such a nanocrystal, the material has properties between that of molecules and bulk, providing a unique opportunity to modify QDs by nanoengineering and altering the composition and size of these tiny structures. By controlling the size and shape parameters, the optical and phonon properties of QDs can be tailored, leading to an optimum heat coupling between the QD and the attached or neighboring protein, DNA, or cell structure and its environment. In addition, in one variation of the subject matter described, denaturing and conformational change of biological important pathogens like bacteria and viruses such as the deadly corona virus family can occur. Finally the described techniques claimed can be applied as well for anti-aging drug development and treatment of aging skin tissue.

The drawings and foregoing description are not intended to represent the only form of the subject matter described herein in regard to the details of the construction and manner of operation. In fact, it will be evident to one skilled in the art that modifications and variations may be necessary without departing from the scope of the subject matter described herein. Although specific terms have been employed, they are intended in generic and descriptive sense only and not for the purpose of limitation.

What is claimed is:

1. A nanobioprocessor for protein and cell therapy comprising:

a quantum dot having selected band gap energies, wherein the quantum dot is coupled or adjacent to at least one protein, cell or tissue; and an electromagnetic radiation source and detector configured to remotely heat or selectively excite the quantum dot to transfer radiation to the at least one coupled or adjacent protein cell or tissue;

wherein the quantum dot is composed with a core of nanocrystals sensitive in the NIR region.

2. The nanobioprocessor of claim 1, wherein the quantum dot is adjacent to a misfolded protein anomalous biomolecule having a conformation that can be changed through at least one of remote vibrational or electronic energy transfer.

3. The nanobioprocessor of claim 1, wherein the quantum dot is adjacent to a misfolded glycoprotein having a conformation that can be changed through at least one of remote vibrational or electronic energy transfer.

4. The nanobioprocessor of claim 1, wherein the protein is a beta-amyloid protein.

5. The nanobioprocessor of claim 1, wherein the nanocrystals are chosen from a group comprising: Pb based-cores, Lead Sulphide (PbS), Lead Selenide (PbSe), Lead Telluride (PbT), and Titanium Oxide.

6. The nanobioprocessor of claim 1, further comprising a micromirror spectrometer for the determination and detection of the radiation transferred to the protein, cell or tissue.

7. The nanobioprocessor of claim 1, wherein the local heating and energy transfer destroys or conforms diseased cells and proteins and also for drug delivery with nanocapsules.

8. The nanobioprocessor of claim 1, wherein the local heating and energy transfer destroys or conforms diseased cells and proteins and also for drug delivery with nanocapsules.

9. A nanobioprocessor for protein and cell therapy comprising:
   a quantum dot having selected band gap energies, wherein the quantum dot is coupled or adjacent to at least one protein, cell or tissue; and
   an electromagnetic radiation source and detector configured to remotely heat or selectively excite the quantum dot to transfer radiation to the at least one coupled or adjacent protein cell or tissue;
   wherein the radiation source is a chosen from a group comprising: NIR infrared diode laser, vertical cavity surface emitting laser, or vertical cavity surface emitting array laser.

10. The nanobioprocessor of claim 9, wherein the quantum dot includes gold particles or gold coated particles with absorption and emission spectra in the NIR region that can be activated by laser pulses to induce heating of the quantum dots and its environment.

11. The nanobioprocessor of claim 9, wherein the laser is tunable in the NIR range.

12. The nanobioprocessor of claim 9, wherein the quantum dot is adjacent to a misfolded protein anomalous biomolecule having a conformation that can be changed through at least one of remote vibrational or electronic energy transfer.

13. The nanobioprocessor of claim 9, wherein the quantum dot is adjacent to a misfolded glycoprotein having a conformation that can be changed through at least one of remote vibrational or electronic energy transfer.

14. The nanobioprocessor of claim 9, wherein the nanocrystals are chosen from a group comprising: Pb based-cores, Lead Sulphide (PbS), Lead Selenide (PbSe), Lead Telluride (PbT), and Titanium Oxide.

15. The nanobioprocessor of claim 9, further comprising a micromirror spectrometer for the determination and detection of the radiation transferred to the protein, cell or tissue.

16. A nanobioprocessor for protein and cell therapy comprising:
   a quantum dot having selected band gap energies, wherein the quantum dot is coupled or adjacent to at least one protein, cell or tissue; and
   an electromagnetic radiation source and detector configured to remotely heat or selectively excite the quantum dot to transfer radiation to the at least one coupled or adjacent protein cell or tissue;
   wherein the quantum dot is coated with lipid layers.

17. The nanobioprocessor of claim 16, wherein the quantum dot is adjacent to a misfolded protein anomalous biomolecule having a conformation that can be changed through at least one of remote vibrational or electronic energy transfer.

18. The nanobioprocessor of claim 16, wherein the quantum dot is adjacent to a misfolded glycoprotein having a conformation that can be changed through at least one of remote vibrational or electronic energy transfer.

19. The nanobioprocessor of claim 16, further comprising a micromirror spectrometer for the determination and detection of the radiation transferred to the protein, cell or tissue.

20. The nanobioprocessor of claim 16, wherein the local heating and energy transfer destroys or conforms diseased cells and proteins and also for drug delivery with nanocapsules.

* * * * *